(12) United States Patent
Tadepalli et al.

(10) Patent No.: US 9,452,569 B2
(45) Date of Patent: *Sep. 27, 2016

(54) FIBER-REINFORCED COMPOSITE ARTICLES MADE FROM FIBERS HAVING COUPLING-INITIATOR COMPOUNDS AND METHODS OF MAKING THE ARTICLES

(71) Applicant: JOHNS MANVILLE, Denver, CO (US)

(72) Inventors: Rajappa Tadepalli, Chennai (IN); Jawed Asrar, Englewood, CO (US); Klaus Friedrich Gleich, Highlands Ranch, CO (US)

(73) Assignee: Johns Manville, Denver, CO (US)

(*) Notice: Subject to any disclaimer, the term of this patent is extended or adjusted under 35 U.S.C. 154(b) by 2 days.

This patent is subject to a terminal disclaimer.

(21) Appl. No.: 14/476,481

(22) Filed: Sep. 3, 2014

(65) Prior Publication Data

US 2016/0023408 A1 Jan. 28, 2016

Related U.S. Application Data

(60) Division of application No. 12/881,736, filed on Sep. 14, 2010, now Pat. No. 8,852,732, which is a continuation-in-part of application No. 12/724,024, filed on Mar. 15, 2010, now Pat. No. 8,378,094, which is a continuation-in-part of application No. 12/008,041, filed on Jan. 8, 2008, now abandoned.

(51) Int. Cl.

| | |
|---|---|
| *C08G 77/04* | (2006.01) |
| *B29C 70/36* | (2006.01) |
| *B29C 70/44* | (2006.01) |
| *C08G 69/48* | (2006.01) |
| *C08L 77/02* | (2006.01) |
| *C08J 5/08* | (2006.01) |
| *C08J 5/24* | (2006.01) |
| *C08G 18/80* | (2006.01) |
| *C03C 25/26* | (2006.01) |
| *B29K 77/00* | (2006.01) |
| *B29L 31/08* | (2006.01) |
| *B29K 105/00* | (2006.01) |
| *B29K 105/12* | (2006.01) |

(52) U.S. Cl.
CPC ............. *B29C 70/36* (2013.01); *B29C 70/443* (2013.01); *C03C 25/26* (2013.01); *C08G 18/8074* (2013.01); *C08G 69/48* (2013.01); *C08J 5/08* (2013.01); *C08J 5/24* (2013.01); *C08L 77/02* (2013.01); *B29K 2077/00* (2013.01); *B29K 2105/0002* (2013.01); *B29K 2105/0014* (2013.01); *B29K 2105/12* (2013.01); *B29L 2031/08* (2013.01)

(58) Field of Classification Search
CPC .............. C08L 77/02; B29K 2105/06; C08G 18/8074; C08J 5/08; C08J 5/24; C03C 25/26
USPC .......................... 428/375, 391; 524/375, 606
See application file for complete search history.

(56) References Cited

U.S. PATENT DOCUMENTS

| | | |
|---|---|---|
| 3,621,001 A | 11/1971 | Steinhofer et al. |
| 4,105,644 A | 8/1978 | Bukac et al. |
| 4,188,478 A | 2/1980 | Goebel, Jr. |
| 4,697,009 A | 9/1987 | Deschler et al. |
| 5,240,974 A | 8/1993 | Lechner et al. |
| 5,782,908 A | 7/1998 | Calahan et al. |
| 5,864,007 A | 1/1999 | Schmid et al. |
| 6,013,855 A | 1/2000 | McPherson et al. |
| 6,040,363 A | 3/2000 | Warner et al. |
| 6,358,557 B1 | 3/2002 | Wang et al. |
| 6,579,965 B2 | 6/2003 | Hoogan et al. |
| 2003/0096904 A1 | 5/2003 | Hakula et al. |
| 2007/0072199 A1 | 3/2007 | Levicky et al. |
| 2007/0166542 A1* | 7/2007 | Braun ................... B29C 73/163 428/402.21 |
| 2008/0241533 A1 | 10/2008 | Dijt et al. |
| 2010/0062238 A1* | 3/2010 | Doyle et al. ............... 428/295.1 |
| 2010/0286343 A1 | 11/2010 | Burghardt et al. |

FOREIGN PATENT DOCUMENTS

| | | |
|---|---|---|
| EP | 0 263 895 A | 4/1988 |
| EP | 0 338 128 A | 10/1989 |
| EP | 0 982 311 A | 3/2000 |
| JP | 08 291186 | 11/1996 |
| JP | 08291186 | * 11/1996 |
| WO | 03084583 | 10/2003 |
| WO | 2008010198 | 1/2008 |

* cited by examiner

*Primary Examiner* — Gregory Listvoyb
(74) *Attorney, Agent, or Firm* — Robert D. Touslee (57) ABSTRACT

Methods of making a fiber-reinforced composite article are described. The methods may include providing fibers to an article template, where the fibers have been treated with a coupling-initiator compound. They may further include providing a pre-polymerized mixture that includes a monomer and a catalyst to the article template. The combination of the fibers and the pre-polymerized mixture may be heated to a polymerization temperature where the monomers polymerize around the fibers and form at least a portion of the composite article. The article may then be removed from the article template. Examples of the fiber-reinforced composite articles may include wind turbine blades for electric power generation.

28 Claims, 4 Drawing Sheets

FIBER-REINFORCED COMPOSITE ARTICLES MADE FROM FIBERS HAVING COUPLING-INITIATOR COMPOUNDS AND METHODS OF MAKING THE ARTICLES

CROSS-REFERENCES TO RELATED APPLICATIONS

This application is a division of prior pending U.S. application Ser. No. 12/881,736 filed Sep. 14, 2010, which is a continuation-in-part of prior U.S. application Ser. No. 12/724,024 filed Mar. 15, 2010 now U.S. Pat. No. 8,378,094 issued Feb. 19, 2013, which is a continuation-in-part of U.S. application Ser. No. 12/008,041 filed Jan. 8, 2008 now abandoned. The entire contents of the above-identified applications are herein incorporated by reference for all purposes.

BACKGROUND OF THE INVENTION

Fiber-reinforced composites are used in a variety of parts and equipment, including automotive parts, boat parts, building elements, and aircraft parts, among other types of articles. One well established method of making these articles is to place the bare fibers in a mold and then flow in the liquid precursors of a thermoset polymer. Once the precursors have infused through the fibers and filled the mold, a curing stage ensues where the precursor polymerize into a thermoset polymer matrix surrounding the fibers. The fiber-reinforced composite may then be released from the mold and, if necessary, shaped, sanded, or otherwise processed into the final article.

Producing fiber-reinforced composites with widely available glass fibers and uncured thermoset resins is inexpensive and usually does not require complex equipment or extreme processing conditions (e.g., high temperatures) to produce the final articles. Still, there are significant disadvantages associated with making fiber-reinforced thermoset articles, as well as deficiencies with the composites in many applications. One considerable disadvantage with making these articles is the health and safety problems posed by working with uncured thermoset resins. These resins often produce a lot of volatile organic compounds (VOCs), many of which are irritants and even carcinogens. Outgasing VOCs are particularly problematic during curing processes when exothermic polymerization reactions raise the temperature of the composite and increase rate which these compounds evaporate into the surrounding atmosphere. In order to prevent VOC concentrations from exceeding safe limits, expensive ventilation and air treatment equipment is required. This equipment is particularly costly and difficult to maintain for the manufacture of larger composite articles, such as boat hulls and wind-turbine blades.

Another significant problem with making fiber-reinforced thermoset composites is the large amounts of unrecyclable waste they generate. Glass reinforced polyester and epoxy wastes do not easily decompose, making them expensive to landfill. When they are contaminated with toxic precursors, such as epoxy prepregs, they present an even greater environmental challenge. The inability to recycle most fiber-reinforced thermosets also presents a disposal challenge when the articles made from these composites reach the end of their useful lives. The size of this challenge only increases with the size of the articles that must be discarded.

Larger-sized articles present additional challenges for thermoset composites. Thermosets in general cannot be welded or melted, which makes it very difficult, if not impossible, to modify or repair thermoset parts once they have been cured. The high degree of crystallinity that is characteristic of many thermoset polymers also makes the composites prone to fractures that cannot easily be repaired. When fractures and other defects form in larger thermoset articles, often the only option is to replace the article at significant cost.

In view of the significant difficulties with both the manufacture and properties of larger articles made from fiber-reinforced thermoset composites, alternative materials are being investigated. One area receiving interest in replacing or blending the thermoset polymers with thermoplastic polymers. Thermoplastics have advantages over thermosets in many article applications, including a usually superior fracture toughness and chemical resistance that can increase the damage tolerance and useable lifetimes in larger articles. The increased toughness of fiber-reinforced thermoplastic composites often means less material is needed to make an article.

Starting monomers for many thermoplastics are less toxic than those of widely used thermosets, and they produce significantly less noxious gases during article production. Many thermoplastics are also meltable and weldable, which allows larger parts to be repaired instead of prematurely replaced. Thermoplastics are generally also recyclable, which significantly decreases environmental impact and waste disposal costs both during manufacturing as well as at the end of an article's lifecycle.

Unfortunately, thermoplastics also have production challenges including significantly higher flow viscosities than uncured thermoset resins. The flow viscosities of widely used thermoplastic polymers may be orders of magnitude higher than uncured epoxy, polyester, and vinylester thermoset resins, which have flow viscosities comparable to water. The higher flow viscosities makes it difficult for thermoplastic resins to infiltrate a fiber mat and produce a homogeneous polymer matrix composite that is free of voids and seams. Oftentimes, it is necessary to introduce the thermoplastic resin under high temperature or high vacuum, which increases the costs and complexity of manufacturing processes. Thus, there is a need for new methods and materials to make fiber-reinforced thermoplastic composites with reduced production problems and improved bonding between the fibers and the polymer matrix. These and other issues are address in the present application.

BRIEF SUMMARY OF THE INVENTION

Embodiments of the invention include methods of making a fiber-reinforced composite article. The methods may include providing fibers to an article template, where the fibers have been treated with a coupling-initiator compound. They may further include providing a pre-polymerized mixture that includes a monomer and a catalyst to the article template. The combination of the fibers and the pre-polymerized mixture may be heated to a polymerization temperature where the monomers polymerize around the fibers and form at least a portion of the composite article. The article may then be removed from the article template.

Embodiments of the invention further include additional methods of making a fiber-reinforced composite article. The methods may include providing a pre-polymerized fiber-containing material comprising fibers in contact with a combination of a monomer and polymerization catalyst, where the fibers have been treated with a coupling-initiator compound. The method may also include applying the pre-polymerized fiber-containing material to an article template, and heating the pre-polymerized fiber-containing material to a polymerization temperature. The monomers polymerize around the fibers to form at least a portion of the composite article.

Embodiments of the invention still further include fiber-reinforced composite articles. The articles may include a thermoplastic polymer matrix and fibers bonded to the thermoplastic polymer matrix by a reacted coupling-initiator compound coupled to the fibers prior to contact with thermoplastic polymer matrix. The coupling-initiator compound initiated the polymerization of the monomer to form the thermoplastic polymer. Examples of the fiber-reinforced composite articles may include wind turbine blades for electric power generation.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Articles made from fiber-reinforced thermoplastic polymer composites are described, as well as methods of making these articles. These articles include, without limitation, equipment and parts for various transportation vehicles such as cars, trucks, boats, aircraft, trains, and non-motorized vehicles such as bicycles and sailboats, among other kinds of transportation vehicles. The articles may further include equipment and parts used in industrial applications, including parts for electric power generation, such as wind turbine blades.

The present composite materials may be used to make large-sized articles that were previously made from a greater number of smaller pieces which were coupled together to make the larger article. The ability of the composites to make the article from a smaller number of pieces, or even a single piece, reduces manufacturing complexity as well as the number of joints, fasteners, and seams that can weaken the overall structural integrity of the article. An exemplary longest dimension for a large article may be about 1 meter or more, about 5 meters or more, about 10 meters or more, about 15 meters or more, about 20 meters or more, about 25, 30, 35, 40, 45, 50, 55, 60, 65, 70, 75, 80, 85, 90, 95, or 100 meters or more, among other ranges of a longest dimension.

The present methods permit the formation of fiber-reinforced composite articles of larger sizes, increased fracture toughness and corrosion resistance, and longer operational lifetimes. These methods include the use of fibers treated with one or more coupling-initiator compounds that react with and populate surfaces of the fibers that are subsequently exposed to the thermoplastic monomers which polymerize to form the polymer matrix of the composite. The coupling end of the coupling-initiator compounds are designed to react with and bond to the fiber, while the more distal oriented initiator can initiate a polymer chain from the surrounding monomers. By initiating polymerization so close to the exposed surfaces of the fibers, and having a significant portion of the polymer directly bonded to the fibers through the coupling-initiator compounds, the fibers are tightly coupled to the surrounding polymer matrix in the composite. This tight coupling is believed to enhance several properties of the articles including increasing their fracture toughness and corrosion resistance.

The present methods also address the problem of high flow viscosities that complicate production processes with thermoplastic polymers. Instead of forming and melting the polymers before incorporating (e.g., injecting) them into the an article mold, the polymers are formed in situ in the mold. This allows the lower viscosity monomers to be incorporated into the mold and infused around the fibers at lower temperatures, in shorter times, and with fewer voids and other defects caused by a slow flowing melted polymer.

The combinations of monomer and coupling-initiator compounds may be selected to have a controllable difference between the melting temperature of the monomer and its polymerization temperature. For example, the melting temperature of the monomer may be lower by about 10° C. or more than its polymerization temperature. This permits the monomer to be melted and incorporated into an article mold for a controlled period of time before increasing the monomer to its polymerization temperature to perform in situ polymerization. It also permits variable control of the timing of the polymerization stage instead of having to work with a fixed, predetermined time of polymerization. For example, inspections and quality checks may be performed to insure the monomer is homogeneously distributed in the mold before the temperature is raised to the polymerization temperature. In contrast, many conventional methods, in particular methods using pre-polymerized thermoset resins, require fixed polymerization times that cannot be significantly accelerated or delayed.

In additional examples, solid monomer (e.g., particles, fiber prepreg, etc.) may be incorporated into the mold at temperatures below the monomer's melting point, before raising the temperature to between the melting and polymerization temperature. This allows the solid monomer to melt and infuse around the fibers and conform to the shape of the mold before being polymerized. Examples may include combinations of adding solid and liquid monomer to a mold at sequential stages prior to polymerization.

Exemplary Methods

Figure 1:
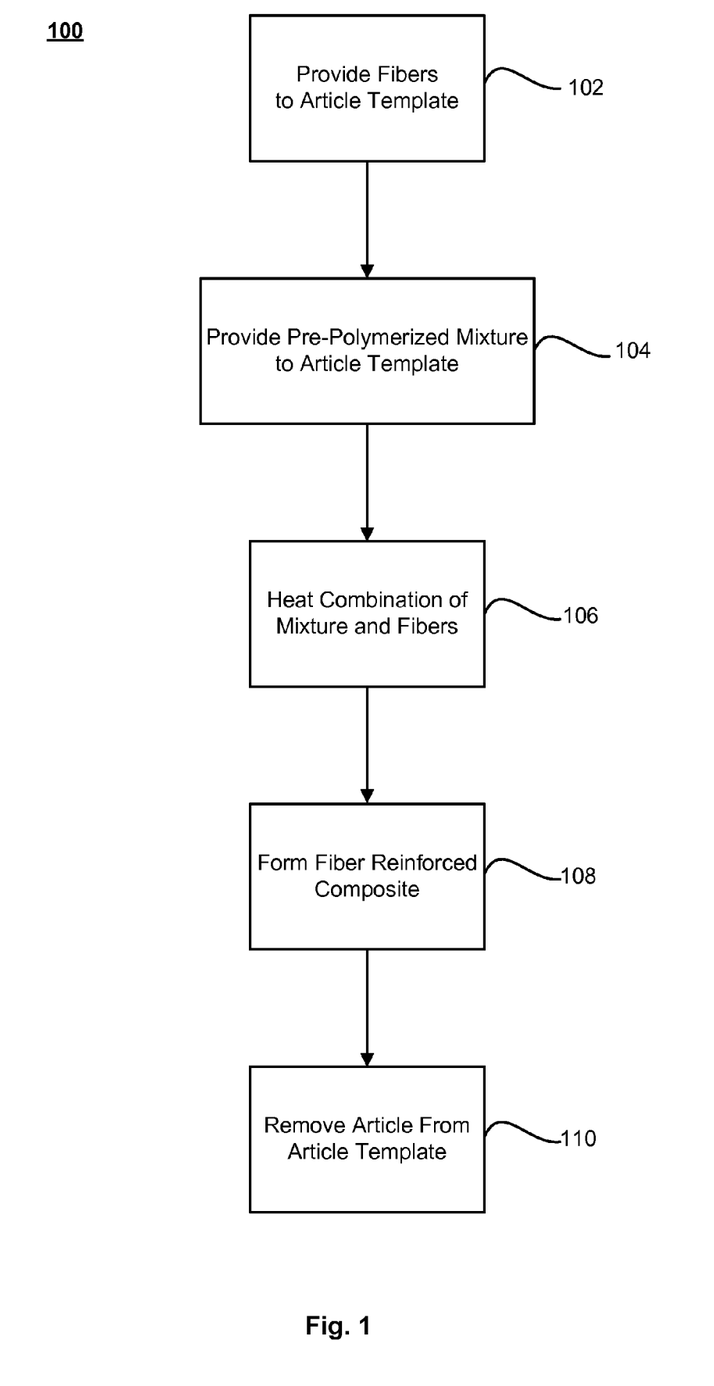
FIG. 1 shows a flowchart with selected steps in methods of making fiber-reinforced composite articles according to embodiments of the invention.

FIG. 1 shows selected steps in an exemplary method 100 of making a fiber-reinforced composite article according to embodiments of the invention. The method 100 may include the step of providing fibers to an article template 102. The fibers are made from a material that can be treated with a coupling-initiator compound to bind the compound to surfaces of the fibers that will be contacted by monomers that help form the polymer matrix. Examples of fibers include glass fibers (e.g., E-glass, etc.), ceramic fibers (e.g., aluminum oxide, silicon carbide, silicon nitride, silicon carbide, basalt, etc.), carbon fibers (e.g., graphite, semi-crystalline carbon, carbon nanotubes, etc.), metal fibers (e.g., aluminum, steel, tungsten, etc.), and polymer fibers (e.g., aramid, etc.). The fibers may be arranged as a mono-axial and/or multi-axial, woven and/or non-woven mat. In addition, the fibers may also include chopped and/or unchopped (i.e., continuous fibers). The mats may have multiple sections with different weave styles, as well as combinations of woven and non-woven sections. In addition, the mats may have regions where chopped fibers are incorporated, for example to allow better wet out and resin penetration in a preselected part or parts of the composite article.

The fibers are treated with one or more coupling-initiator compounds whose coupling moieties can react with portions of the fibers to bind together the fibers and reacted compounds. In some contexts, a coupling-initiator compound may be referred to as a sizing compound that enhances the binding between the fibers and surrounding polymer matrix. The coupling-initiator compound may also be referred to as an activator compound that starts the polymerization of the surrounding monomer is close proximity to the fiber surface.

Specific coupling-initiator compounds may be selected based on the type of fiber and thermoplastic used in the composite. Generally speaking, the coupling-initiator compounds may have the formula C—X—(I)$_n$, where C represents the coupling moiety, (I)$_n$ represents n polymerization initiator moieties, and X represents a linking moiety that links the C moiety to the one or more I moieties. When the fibers are glass fibers, the coupling moiety C may include one or more silicon groups, and the coupling-initiator compound may be represented by the formula S—X—(I)$_n$, where S represents a silicon-containing coupling moiety and X and (I)$_n$ have the same meaning as described above.

The method 100 may further comprise providing a pre-polymerized thermoplastic mixture to the article template 104. The pre-polymerized mixture may include monomers and/or oligomers of the thermoplastic and/or a polymerization catalyst, among other components. The pre-polymerized mixture may also include partially polymerized compounds such as dimers, trimers, and/or oligomers of the thermoplastic. The pre-polymerized mixture may be added in the liquid phase to the article template, or added in the solid phase. When the mixture is added in the liquid phase, it has a temperature at or above the melting point of the thermoplastic monomers and other components, but below a temperature where significant polymerization of the monomers occur. When the mixture is added in the solid phase, it may be added as particles to the article template and/or exist as a pre-impregnated ("pre-preg") coating on the fibers that are added to the template. Embodiments further include providing the pre-polymerized polymer mixture as both a liquid-phase mixture and solid-phase mixture to the article template.

In liquid-phase additions the monomer and the polymerization catalyst may be kept separate until they are provided to the article template. For example, the catalyst may be combined with the liquid-phase monomer immediately before or during there introduction (e.g., injection) into the article template. Alternatively, the monomer and catalyst may be combined and stored as a solid or liquid pre-polymerized mixture well before their introduction to the article template. While the liquid and solid phase mixtures of the pre-polymerized thermoplastic combined with catalyst may exhibit some degree of polymerization—for example the formation dimers, trimers, and/or other oligomers—they are still considered pre-polymerized mixtures since full polymerization initiated by a coupling-initiator compound has not occurred. Similarly, pre-preg fibers that have a coating of B-stage thermoplastic materials surrounding the fibers may still be considered a pre-polymerized mixture or a component of the pre-polymerized mixture. For purposes of this application, the discussions of polymerizations of the monomers may also cover polymerizations of dimers, trimers, and/or other oligomers of the thermoplastic.

Examples of thermoplastic polymers whose monomers may be included in the pre-polymerized polymer mixture may include polybutylene terephthlalate (PBT), polyethylene terephthalate (PET), polyamide-6 (PA-6), polyamide-12 (PA-12), polyamide-6,6 (PA-6,6), cyclic poly(1,4-butylene terephthalate) (CBT), polyurethanes (TPU), polymethylmethacrylate (PMMA), polycarbonates (PC), polyphenylenesulphide (PPS), polyethylenenapthalate (PEN), polybutylenenaphthalate (PBN), polyether etherketone (PEEK), and polyetherketoneketone (PEKK), and combinations of two or more of these polymers, among other polymers.

One exemplary pre-polymerized polymer mixture includes lactam monomers that produce polyamide (also called nylon) when polymerized. The lactam monomers may have the formula:

where R represents a $C_3$ to $C_{12}$ substituted or unsubstituted cyclic hydrocarbon chain. The polymerization of these lactam monomers involves the opening of the cyclic hydrocarbon chain to make a linear chain with reactive carbonyl and amine groups separated by a —(CH$_2$)$_n$— hydrocarbon group.

One exemplary lactam monomer that enjoys wide commercial use is caprolactam, which polymerizes into nylon 6. Other lactam monomers may include butyrolactam (also known as 2-pyrrolidone) which polymerizes into nylon 4; valerolactam which polymerizes into nylon 5; capryllactam which polymerizes into nylon 8; and lauryllactam which polymerizes into nylon 12; among other lacatams.

After the pre-polymerized mixture is provided to the article template and made sufficient contact with the fibers, the combination of mixture and fibers may be heated to a temperature where significant polymerization of the monomers occur, as shown in step 106. In an example where caprolactam is the monomer, the temperature of the pre-polymerized mixture may be raised from a melting temperature of between about 80° C. and 120° C., to a polymerization temperature of about 120° C. or more (e.g., about 120° C. to about 220° C.). In additional examples, the pre-polymerized mixture may have a melting temperature of about 80° C. to about 200° C. (e.g., about 100° C. to about 160° C.), and may have a polymerization temperature of about 120° C. to about 220° C. (e.g., about 180° C. to about 220° C.).

At the polymerization temperature, the polymerization-initiator moieties facilitate polymerization around the fibers.

In the case of lactam monomers for example, the initiator moieties may have the formula:

where the carbonyl group is bonded to a linking moiety of the coupling-initiator compound and R represents a $C_3$ to $C_{12}$ substituted or unsubstituted cyclic hydrocarbon chain. When the combination of the pre-polymer lactam mixture and fibers is raised to the polymerization temperature, the ring structure may open or be otherwise activated to initiate a branched or unbranched polymerized chain from the initiator moiety. The chain is coupled directly to the fiber through the coupling moiety and linking moiety trunk of the coupling-initiator compound.

The polymerization of the lactam monomers may be facilitated by cationic catalysts, anionic catalysts, and/or water. In cationic polymerizations, the catalyst may be an acid that protonates the carbonyl oxygen and/or nitrogen group on the lactam to start a nuclephilic reaction between the protonated monomer and a second lactam monomer. This reaction may be followed by a series of ring-opening acylations of the primary amine to build the polyamide chain.

In anionic polymerizations, the catalyst may include a base such as an alkali metal, alkali-earth metal hydroxide, or alkali metal amide (among other bases) that deprotonates the lactam nitrogen to form an anion that reacts with a second lactam monomer. Subsequent proton transfer and propagation reactions build the polyamide chain. In some instances, the reaction between the initial anion and the second lactam monomer may be further facilitated by an activator compound, such as an acyl halide or anhydride (among other activators).

In hydrolytic polymerizations that involve water, polymerization may be initiated when the water initiates a hydrolysis reaction that opens the lactam ring to form an amino acid. The amine group of the amino acid then reacts with additional lactam monomers in subsequent ring-opening reactions to build the polyamide chain.

At least a portion of the polymer matrix formed by the polymerization of the lactam monomers is initiated by the initiator moieties on the coupling-initiator compounds bound to the treated fibers. These moieties start the formation of straight and/or branched polyamide polymers who formation is also aided by the one or more catalysts present. The coupling-initiator compounds create a covalently-bonded link between the surface of the fibers and the surrounding polymers that is significantly stronger than a bond formed by simply curing a polyamide resin in the presence of untreated fibers.

The present polymer matrices may also include polymers that are not directly bonded to the treated fibers. These polymers may have been formed, for example, through polymerizations that were not initiated at an initiator moiety, and polymers that have fragmented or decoupled after polymerization was initiated at the moiety. Although these polymers may not be directly bonded to the fibers, their columbic and physical interactions with the directly bonded polymers may further strengthen the bonding between the treated fibers and the surrounding polymer matrix.

As the polymerization of the monomers around the fibers progress, a fiber-reinforced composite is formed in the article template. The composite material may form a portion or whole of the composite article 108. The shape of the composite article may be defined, at least in part, by the shape of the article template, which acts as a mold. For example, the article template may be shaped such that the composite forms front or back half of a wind turbine blade that are joined in subsequent production steps. Alternatively, the article template may be designed for a one-shot fabrication of the composite article (e.g., forming both halves of the blade from a single article template).

When the composite material has had sufficient time to solidify, it may be removed from the article template 110. In some instances, removal may be facilitated by applying release agents to the surfaces of the article template that are exposed to the fibers and pre-polymerized mixtures that form the composite article. These release agents hinder the fibers and polymerizing monomers from binding with the template as the composite is formed.

The composite material may be removed from the template either before or after the polymer matrix has fully formed. In instances where the composite material is removed before curing is completed, the curing has progressed to the point where the article is sufficiently solid to retain the shape of the article after removal from the template. The removed article may undergo subsequent processing steps, such as sanding, cutting, polishing, washing, drilling, coating, and/or painting, among other post-formation steps. In the case where the composite is a portion of an article, the removed article may undergo steps to form the whole article, such as gluing, gap filling, and/or fastening the composite to other components to make the whole article.

Figure 2:
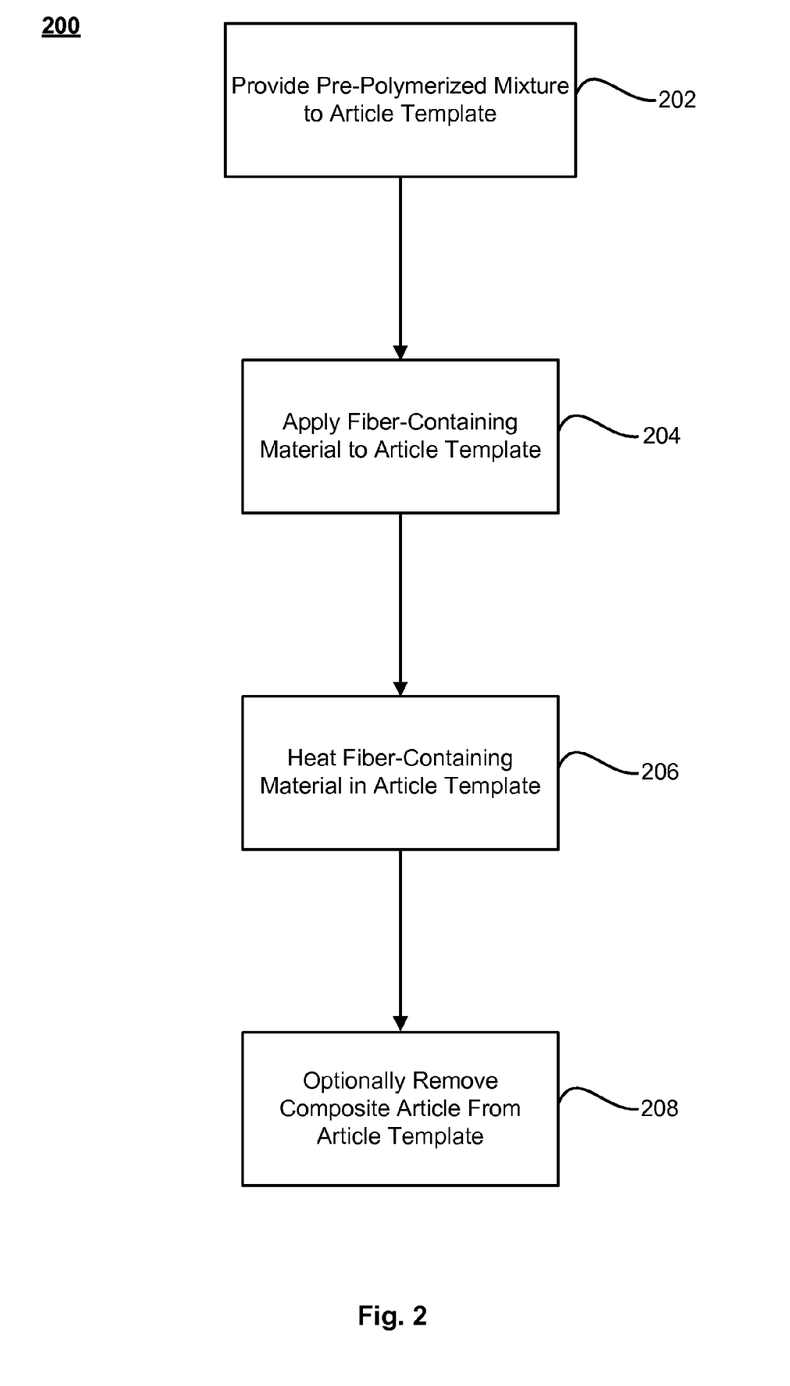
FIG. 2 shows a flowchart with selected steps in additional methods of making fiber-reinforced composite articles according to embodiments of the invention.

Referring now to FIG. 2, a flowchart outlines selected steps in additional methods of making fiber-reinforced composites according to embodiments of the invention. The methods 200 may include providing a pre-polymerized fiber containing material (e.g., a pre-preg), where the fibers are in contact with a combination of the pre-polymerized thermoplastic (e.g., monomers, oligomers) and a polymerization catalyst 202. Examples of the pre-polymerized fiber may include glass fibers that have been pre-treated with a coupling-initiator compound and coated with a pre-polymerized mixture of monomer and polymerization catalyst. The pre-polymerized mixture may be applied above a melting temperature for the monomers, but below a temperature where significant polymerization of the monomers occur. Following the application of the monomers, the treated fibers may be cooled to solidify the coating and stored until use.

That use may include applying the pre-polymerized fiber-containing material to an article template 204 that may act as a mold for a composite article. The pre-polymerized fiber-containing material may be applied as a lay-up of fiber materials in the article template. In some embodiments the fibers may be arranged in a fiber mat before being applied to the template, or arranged to have a particular orientation or set of orientations during and/or after being layed-up in the template.

The methods 200 may optionally include applying additional layers of fiber-containing material to the article template. These additional layers may consist of untreated fibers, fibers treated with coupling-initiator compounds that are not in contact with a pre-polymerized mixtures, and additional layers of pre-polymerized fiber-containing material. The fiber layers may be stacked on top of each other, and/or may be applied side-by-side in the article template. Embodiments may include positioning the pre-polymerized fiber-containing material in specific locations of the article template to enhance the strength and mass of the composite material in those areas. For example, one or more layers (or sections of layers) of the pre-polymerized fiber-containing material may be positioned where the outer shell (i.e., skin) of wind turbine blade makes contact with an internal support structure of the blade such as a rib and/or spar.

The methods 200 may also optionally include providing a pre-polymerized mixture of monomers and polymerization catalyst to the article template following the lay-up of the fiber-containing materials. The pre-polymerized mixture may be a combination of melted monomers/oligomers and catalyst provided to the fiber materials in the article template by, for example, resin transfer molding (RTM), vacuum-assisted resin transfer molding (VARTM), among other techniques.

After the pre-polymerized fiber-containing material (and any additional materials) have been applied to the article template, the materials may be heated to a temperature where the monomers polymerize to form a composite material 206. The polymerization processes include the activation of an initiator moiety on a coupling-initiator compound that has been bound to the treated fiber. These moieties start the formation of polymers (e.g., polyamide polymers) that may be covalently linked to the fibers, strengthening the bond between the fibers and the surrounding polymer matrix. The composite material that results from the polymerization processes may form either a portion or whole of a fiber-reinforced composite article.

In some embodiments, the article template (or a portion thereof) may become part of the composite article. In these embodiments, the fiber-reinforced composite is bonded to one or more surfaces of the article template that were exposed to the pre-polymerized fiber-containing material. The composite article that is formed includes an outer layer made from the article template. In additional embodiments, the fiber-reinforced composite may optionally be removed from the article template 208, and the template may be discarded or prepared for forming another composite article.

Exemplary Methods of Making a Wind Turbine Blade

Figure 3:
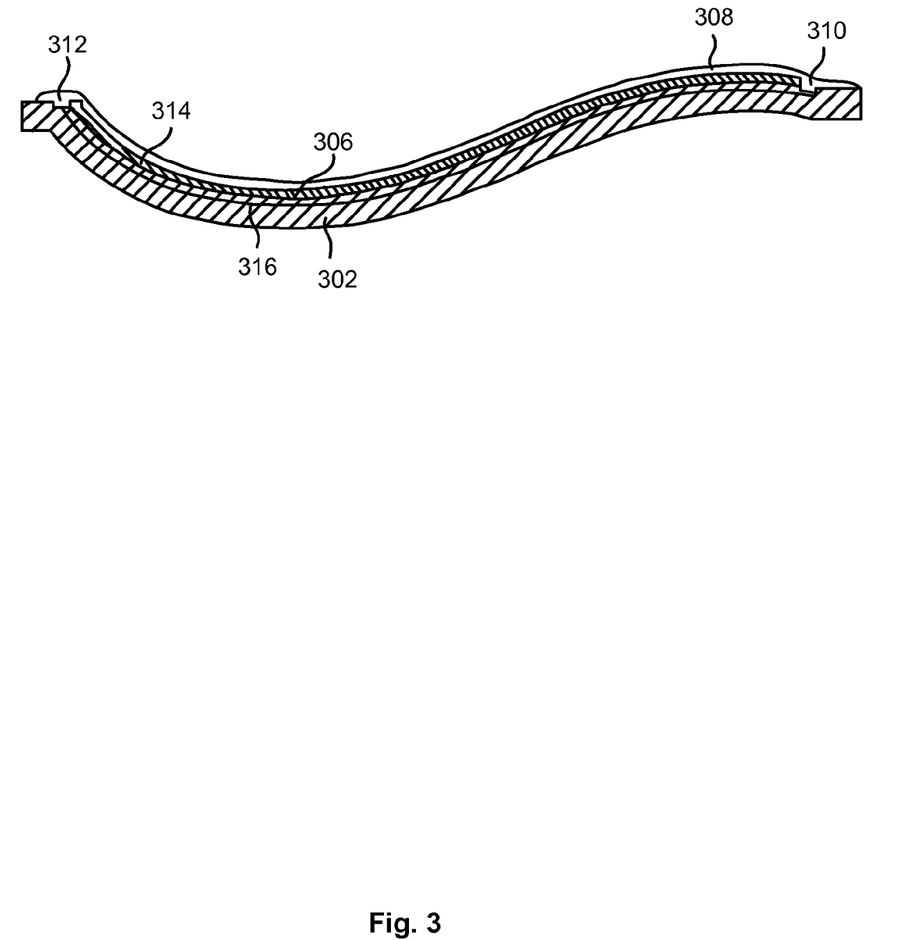
FIG. 3 illustrates a simplified cross-sectional drawing of an article template for making a wind turbine blade according to embodiments of the invention.
Figure 4:
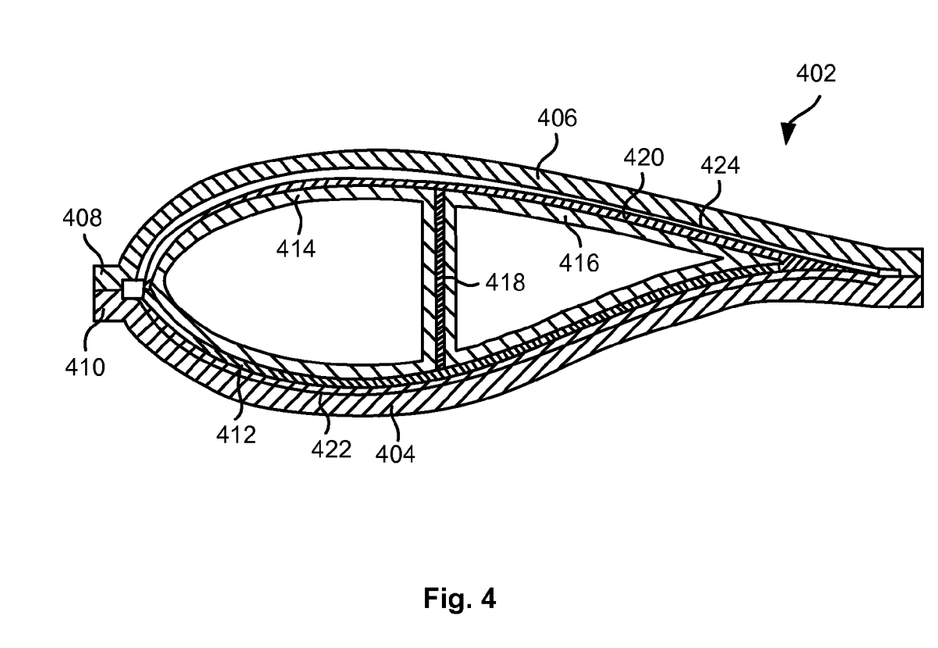
FIG. 4 illustrates a simplified cross-sectional drawing of an article template for a one-shot method of making a wind turbine blade according to embodiments of the invention.

Exemplary methods of making a wind turbine blade will now be described with reference to the article templates shown in FIGS. 3 and 4 respectively. FIG. 3 shows an article template 302 for part of the outer skin of a wind turbine blade made from a fiber reinforced composite. The template 302 may be for the side of the blade which faces the wind during operation of the turbine. A second article template (not shown) is used to form the opposite side of the blade. The two skins may then be joined using fasteners, adhesives, gap fillers, etc. to form the outer surface of the blade. Internal blade components, such as spars and ribs, may also be added when the skins are joined together.

The article template 302 may be made from a rigid material that has an inner surface 306 defining the shape of the outer skin. This surface may be made from a material or treated (e.g., coated) to form a exposed layer of material that facilitates the release of the fiber-reinforced composite outer skin from the article template 302.

The article template 302 may further comprise a vacuum bag 308 that may be fluid-tightly sealed to the peripheral edges of the template. Together, the liner of the vacuum bag 308 and inner surface 306 define an enclosed volume where the materials for the composite may be combined and heated to form the fiber-reinforced composite outer skin.

The article template 302 may further include openings 310 and 312, through which pre-polymerized liquid mixtures of monomer and catalyst may flow to make contact with the fiber materials shown in fiber layer 314. As noted above, additional pre-polymerized materials (e.g., solid pre-preg materials) may also be present with the fibers in the fiber layer 314.

When the vacuum bag 308 is evacuated, the change in air pressure between the inside and outside of the vacuum bag 308 may press the bag liner against the fiber layer 314. In addition, a pressure differential causes the pre-polymerized mixture to flow through openings 310 and 312 to infiltrate the fiber layer 314. In the embodiment shown, the flowing mixture may form two fluid fronts at the forward and read ends of the outer skin which may converge proximate to the middle of the skin. Additional flow configurations are possible depending upon the number and positioning of the openings in the article template.

When the pre-polymerized mixture has been distributed over the fiber layer 314, the materials may be heated to a polymerization temperature to start the formation of the fiber-reinforced composite. The heating may, for example, be carried out by a heating element 316 positioned proximate to the inner surface 306 of the article template 302. When the polymerization process is sufficiently advanced, the nascent composite may be allowed to cool at a pre-defined rate to ensure the outer skin is formed with the requisite mechanical properties. The outer skin may then be removed from the article template 302 so that it can be combined with the other parts of the blade. The article template may be treated (e.g., cleaned and prepared) to form another outer skin.

The article template 302 shown in FIG. 3 forms only a part of the outer skin of a wind turbine blade. FIG. 4 shows an article template 402 that is designed to form a more complete outer skin for a wind turbine blade with a one-shot manufacturing technique. The article template 402 includes a first mold component 404 and a second mold component 406 which are combined to form the one-shot article template 402. The first and second mold components may have peripheral edges 408, 410 that can be joined to form an air-tight seal.

One-shot methods of making a wind turbine blade with article template 402 may include laying-up fiber materials in the first mold component 404 to form a first fiber layer 412 in the component. Additional materials such as particles of pre-polymerized monomer and catalyst, may also be added to the mold component 404 and/or fiber layer 412. First and second internal support sections 414, 416 may be placed in the first mold component 404 over the first fiber layer 412. The first and second internal support sections 414, 416 may be made from rigid materials such as wood, ceramic, lightweight metal or alloy, and/or polymers, among other materials. The rigid material may be surrounded by a more flexible material (e.g., foam rubber) and a flexible membrane that may make contact with the fiber layers in the template 402.

An additional fiber layer 418 may support a gap between the first and second support sections 414, 416. This fiber layer 418 may be converted into an internal support of the final composite that joins opposite sides of the blade for increased strength and stability. In additional embodiments, two or more internal supports (or conversely no supports) may be formed in blade.

Another additional fiber layer 420 may be layed-up over the first and second fiber support structures 414, 416 such that the ends of the fiber layer 420 overlap or otherwise contact the complementary ends of first fiber layer 412. The second mold component 406 may then be placed over the fiber layers and internal supports and secured to first mold component 404 along the peripheral edges 408, 410.

Openings (not shown) in the article template 402 may be coupled to vacuum lines that create vacuum channels in the enclosed spaces between the mold components 404, 406, and outer surfaces of support sections 414, 416. When the channels are evacuated, positive pressure exerted from inside the support sections 414, 416 may push their outer flexible membranes into the surrounding fiber layers 412, 420 to press them against inside surfaces of the article template 402. The evacuation of the channels also creates a pressure gradient for the flow of a pre-polymerized mixture through the fiber layers.

Following the addition of the pre-polymerized materials with the fiber layers, the combination may be heat cured to polymerize the monomers and form the fiber reinforced composite article. The heating may be done by a heat transfer system 422, 424, such as heating filaments integrated into the first and second mold components 404, 406.

Once the composite article has sufficiently cured, the mold components 404, 406 may be separated and the fiber-reinforced composite wind turbine blade removed from the article template 402.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the fiber" includes reference to one or more fibers and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of making a fiber-reinforced composite article, the method comprising:
providing fibers to an article template, wherein the fibers have been treated with a coupling-initiator compound and the coupling-initiator compound has the formula:

$$S-X-(I)_n$$

wherein:
n is an integer having a value between 1 and 5,
S comprises a silicon-containing coupling moiety through which the coupling-initiator compound bonds to a substrate surface on the fibers,
X comprises a linking moiety to link the S moiety with the one or more I moieties,
$(I)_n$ comprises one or more polymerization initiator moieties,
each of the initiator moieties is capable of initiating a polymerization of a monomer at the polymerization temperature, and
each of the initiator moieties is the same or different;
providing a pre-polymerized mixture comprising the monomer and a catalyst to the article template;
heating a combination of the fibers and the pre-polymerized mixture to a polymerization temperature where the monomers polymerize around the fibers and form at least a portion of the composite article, wherein the portion of the composite article comprises a thermoplastic polymer; and
removing the composite article from the article template.

2. The method of claim 1, wherein at least one of the initiator moieties (I), comprises an organo-cyclic ring having the formula:

wherein represents a $C_3$ to $C_{12}$ substituted or unsubstituted cyclic hydrocarbon chain.

3. The method of claim 2, wherein at least one of the initiator moieties $(I)_n$ has the formula:

4. The method of claim 1, wherein the monomer comprises a lactam and the polymerized monomers comprise a polyamide.

5. The method of claim 4, wherein the lactam monomer comprises caprolactam and the polyamide comprises nylon 6.

6. The method of claim 1, wherein the catalyst comprises a salt of a lactam, wherein the salt is an alkali metal salt or an alkali-earth metal salt.

7. The method of claim 6, wherein the catalyst comprises magnesium bromide caprolactam.

8. The method of claim 1, wherein the pre-polymerized mixture is provided as a liquid to the article template and infused around the fibers to form the combination of the fibers and the pre-polymerized mixture.

9. The method of claim 1, wherein at least a portion of the pre-polymerized mixture provided to the article template includes solid particles comprising the monomer and the catalyst.

10. The method of claim 1, wherein the method further comprises:
applying a solid-phase pre-polymerized fiber-containing material to the article template, wherein the pre-polymerized fiber-containing material comprises fibers in contact with a combination of the monomer and the polymerization catalyst, and wherein the fibers have been treated with the coupling-initiator compound, and
wherein the pre-polymerized fiber-containing material is heated with the combination of the fibers and the pre-polymerized mixture to form at least a portion of the composite article.

11. The method of claim 10, wherein the method further comprises heating the pre-polymerized fiber-containing material to a melting temperature where the monomer melts but does not polymerize; and
infusing the molten monomer around the fibers before raising the pre-polymerized fiber-containing material to the polymerization temperature.

12. The method of claim 1, wherein the method further comprises adding more of the monomer to the to the article template after providing the pre-polymerized mixture to the article template.

13. The method of claim 12, wherein more of the polymerization catalyst is added with the additional monomer.

14. A fiber-reinforced composite article comprising:
a thermoplastic polymer matrix; and
fibers bonded to the thermoplastic polymer matrix by a reacted coupling-initiator compound coupled to the fibers prior to contact with thermoplastic polymer matrix, wherein the coupling-initiator compound initiated the polymerization of the thermoplastic polymer, and the coupling-initiator compound has the formula:

wherein:
n is an integer having a value between 1 and 5,
S comprises a silicon-containing coupling moiety through which the coupling-initiator compound bonds to a substrate surface on the fibers,
X comprises a linking moiety to link the S moiety with the one or more I moieties,
(I)$_n$ comprises one or more polymerization initiator moieties,
each of the initiator moieties is capable of initiating a polymerization of the monomer at the polymerization temperature, and
each of the initiator moieties is the same or different.

15. A process for preparing a reinforced resin material comprising the steps of:
providing an inorganic substrate;
applying to the inorganic substrate a sizing composition comprising a coupling activator compound of the formula:

wherein:
X and Y comprise linking moieties to link the S moiety with the I moiety, and
R$^3$, R$^4$, and R$^5$ are the same or different, and are selected from the group consisting of an alkyl group, an aryl group, an alkoxy group, a halogen group, and an alkylcyclic group;
mixing the sized inorganic substrate with a monomer and a polymerization catalyst to form a polymerization mixture; and
exposing the polymerization mixture to conditions sufficient to cause polymerization of the monomer to form a reinforced resin in which the inorganic substrate is coupled to the surrounding polymer matrix.

16. A method of making a fiber-reinforced composite article, the method comprising:
providing a pre-polymerized fiber-containing material comprising fibers in contact with a combination of a monomer and polymerization catalyst, wherein the fibers have been treated with a coupling-initiator compound;
applying the pre-polymerized fiber-containing material to an article template;
heating the pre-polymerized fiber-containing material to a polymerization temperature where the monomers polymerize around the fibers to form at least a portion of the composite article; and
wherein the coupling-initiator compound has the formula:

wherein n is an integer having a value of 2 or more;
S comprises a silicon-containing coupling moiety through which the coupling-initiator compound bonds to a substrate surface on the fibers;
X comprises a linking moiety to link the S moiety with the 2 or more I moieties; and
(I)$_n$ comprises 2 or more polymerization initiator moieties, wherein each of the initiator moieties is capable of initiating a polymerization of the monomer at the polymerization temperature, and wherein each of the initiator moieties is the same or different.

17. The method of claim 16, wherein the method further comprises removing the composite article from the article template.

18. The method of claim 16, wherein the composite article further comprises at least a portion of the article template.

19. The method of claim 16, wherein the combination of the monomer and polymerization catalyst is a solid at room temperature, and the pre-polymerized fiber-containing material is solid when applied to the article template.

20. The method of claim 19, wherein the method comprises:
heating the solid pre-polymerized fiber-containing material to a melting temperature where the monomer melts but does not polymerize; and
infusing the molten monomer around the fibers before raising the pre-polymerized fiber-containing material to the polymerization temperature.

21. The method of claim 16, wherein the method further comprises adding more of the monomer to the to the article template after applying the pre-polymerized fiber-containing material to the article template.

22. The method of claim 16, wherein the monomer comprises a lactam and the polymerized monomers comprise a polyamide.

23. The method of claim 22, wherein the lactam monomer comprises caprolactam and the polyamide comprises nylon 6.

24. A method of making a fiber-reinforced composite article, the method comprising:
   providing a pre-polymerized fiber-containing material comprising fibers in contact with a combination of a monomer and polymerization catalyst, wherein the fibers have been treated with a coupling-initiator compound;
   applying the pre-polymerized fiber-containing material to an article template;
   heating the pre-polymerized fiber-containing material to a polymerization temperature where the monomers polymerize around the fibers;
   removing the composite article from the article template; and
   wherein the coupling-initiator compound has the formula:

wherein n is an integer having a value of 2 or more;
   S comprises a silicon-containing coupling moiety through which the coupling-initiator compound bonds to a substrate surface on the fibers;
   X comprises a linking moiety to link the S moiety with the 2 or more I moieties; and
   $(I)_n$ comprises 2 or more polymerization initiator moieties, wherein each of the initiator moieties is capable of initiating a polymerization of the monomer at the polymerization temperature, and wherein each of the initiator moieties is the same or different.

25. The method of claim 24, wherein the combination of the monomer and polymerization catalyst is a solid at room temperature, and the pre-polymerized fiber-containing material is solid when applied to the article template.

26. The method of claim 24, wherein the method further comprises adding more of the monomer to the to the article template after applying the pre-polymerized fiber-containing material to the article template.

27. The process of claim 15, wherein the coupling activator is

28. The process of claim 15, wherein the coupling activator is

* * * * *